United States Patent

Wu et al.

[11] Patent Number: 5,985,121
[45] Date of Patent: Nov. 16, 1999

[54] FAST SAMPLING DEVICE AND SAMPLING METHOD FOR CAPILLARY ELECTROPHORESIS

[76] Inventors: Jiaqi Wu, 17 Marlow Crescent, Markham, Ontario, Canada, L3R 4P4; Janusz B. Pawliszyn, 383 Dunvegan Drive, Waterloo, Ontario, Canada, N2K 1W7

[21] Appl. No.: 08/644,860

[22] Filed: May 10, 1996

[51] Int. Cl.$^6$ .................................................. G01N 27/26
[52] U.S. Cl. ............................................................ 204/601
[58] Field of Search .................................. 204/451, 453, 204/601, 604

[56] References Cited

U.S. PATENT DOCUMENTS

| | | | |
|---|---|---|---|
| 5,194,133 | 3/1993 | Clark et al. | 204/608 |
| 5,324,401 | 6/1994 | Yeung et al. | 204/452 |
| 5,395,502 | 3/1995 | Pawliszyn | 204/603 |
| 5,480,526 | 1/1996 | Liao et al. | 204/451 |
| 5,492,838 | 2/1996 | Pawliszyn | 436/178 |

FOREIGN PATENT DOCUMENTS

| | | |
|---|---|---|
| 05072178 | 3/1993 | Japan . |
| 06118058 | 4/1994 | Japan . |
| 96/33405 | 10/1996 | WIPO . |

OTHER PUBLICATIONS

JAPIO abstract of JP05072178 (Kanabara Hideki), Mar. 23, 1993.
WPIDS abstract of JP06118058 (Kanae et al.), Apr. 28, 1994.
"Capillary Ultrafiltration: In Vivo Sampling Probes for Small Molecules", Anal. Chem. 1992, 64, 2831–2835, (Linhares and Kissinger).
"Isoelectric focusing in capillaries and slab gels: A Comparison", J. Cap. Elec. 001 : 1 1994 (Righetti and Gelfi).
"New Approaches to Capillary Isoelectric Focusing of Proteins", Bio/Technology vol. 12 408–409 (1994) (Schwartz and Pritchett).
Beckman Instruments Commercial Brochure A–1771 "Application Information", pp. 1–4, entitled Hemoglobin Analysis by Capillary Isoelectric Focusing (CIEF) (Hempe).
"A Capillary Cartridge with an On–line Desalting Device . . ." in *Analytical Chemistry*, vol. 67, No. 13, Jul. 1, 1995 (Wu and Pawliszyn).
"Two–Dimensional Gel Electrophoresis/Liquid Chromatography . . . " in Anal. Chem. 1994, 66, 2529–2536 (Rose and Opiteck).
"Membrane–Based On–Column Mixer for Capillary Elector–phoresis/Electrochemistry" in Anal. Chem. 1995, 67, 13–18 (Zhou and Lunte).
"On–line dialysis as a sample–preparation technique for column liquid chromatography" in trends in analytical chemistry, vol. 12, No. 6, 1993 (Merbel and Brinkman).

*Primary Examiner*—Robert Warden
*Assistant Examiner*—Alex Noguerola
*Attorney, Agent, or Firm*—Ridout & Maybee

[57] ABSTRACT

An improved apparatus and method for the capillary electrophoretic separation of chemical compounds comprises carrying out on-line sample preparation by means of semipermeable membranes connected to the capillary separation column for selective introduction of ampholytes into the capillary separation column. Semipermeable membrane means may also be used on-line for preliminary desalting of the sample prior to its introduction into the separation column.

8 Claims, 6 Drawing Sheets

FIG. 6

FAST SAMPLING DEVICE AND SAMPLING METHOD FOR CAPILLARY ELECTROPHORESIS

This invention relates to semipermeable membrane-based sampling apparatus for use in the separation of chemical compounds by capillary electrophoresis (CE) techniques, such as CE using gel-filled or packed capillary separation columns, capillary zone electrophoresis (CZE), and capillary isoelectric focusing (CIEF). Semipermeable membranes are employed, in an apparatus according to the present invention, to effect the on-line separation of target analytes from a sample matrix and to permit these analytes to enter the capillary separation column.

In a further aspect, the invention relates to an improved method of introducing an analyte sample into the capillary separation column of apparatus for carrying out capillary electrophoresis.

In a preferred embodiment, apparatus according to the present invention is used in the separation of ionizable biological molecules such as proteins and peptides by capillary isoelectric focusing (CIEF), the apparatus including a capillary separation column tipped with sections of dialysis hollow fiber.

According to a further aspect of the invention, the sampling apparatus includes a semipermeable membrane-based on-line desalting carrier ampholytes mixing device. Used in conjunction with a real-time absorption imaging detection system including a charged-couple-device (CCD) camera, the sampling means and associated on-line desalting device of the present invention allow for very short total analysis times to be achieved in capillary electrophoretic separations.

BACKGROUND OF THE INVENTION

The publications referred to in what follows and identified by footnotes are incorporated by reference herein for their teachings as to capillary electrophoretic techniques.

Capillary electrophoresis (CE) has been established as an important separation method in bioanalytical chemistry. Separation and detection of very small amounts of biological samples, about pL-nL volumes, can be achieved with CE. This is generally not possible with more conventional separatory methods, even high performance liquid chromatography (HPLC). There are several CE separation methods in use for different kinds of samples. They include capillary zone electrophoresis, moving boundary capillary electrophoresis, capillary isotachophoresis and capillary isoelectric focusing.

Isoelectric focusing (IEF) is a special electrophoretic technique for separating amphoteric substances such as peptides and proteins in an electric field, across which there is both a voltage and a pH gradient, acidic in the region of the anode and alkaline near the cathode. Each substance in the mixture will migrate to a position in the separation column where the surrounding pH corresponds to its isoelectric point. There, in zwitterion form with no net charge, molecules of that substance cease to move in the electric field. Different amphoteric substances are thereby focused into narrow stationary bands.

Capillary isoelectric focusing (CIEF) is becoming recognized as a powerful separation technique for proteins and peptides due to its fast separation speed and ease of use for quantitative determination.[1] Until now most applications of CIEF have been done using commercial capillary electrophoresis (CE) instruments. These instruments have a 20–60 cm long capillary and an on-column UV absorption detector. When using these instruments for CIEF, all protein zones separated by the focusing process must be moved through the detection point of the on-column detector located at one end of the capillary. Isoelectric focusing can be done in commercial CE instruments by a "two step" method or a "one step" method.

In the "two step" method, the capillary inner wall is coated with non-cross-linked acrylamide to eliminate electroosmotic flow.[2] The capillary is first filled with mixture of sample and carrier ampholytes, and two electrolyte reservoirs connected to the capillary ends are filled with anolyte and catholyte, respectively. Then, a DC voltage is applied across the capillary. After the focusing process finishes, all protein zones are stationary inside the capillary. Finally, a mobilization process is used to move all these zones through the detection point. Mobilization can be achieved by using hydrodynamic force[2] or adding salts[2,3] to one end of the capillary column.

In the "one step" method, an uncoated capillary is used as the separation column. A plug of sample and carrier-ampholytes solution is introduced into the capillary between anolyte and catholyte. Additives, such as methylcellulose, are mixed into sample and electrolyte solutions to increase viscosity of the solution and reduce the electroosmotic flow.[4,5] Upon application of a DC voltage, protein components are focused inside the capillary while the whole volume of solutions inside the capillary is mobilized slowly from the anodic end to the cathodic end.

The "one step" method appears to have advantages over the "two step" method since it overcomes many problems of the "two step" method, such as blind section in the capillary,[3] and the instability of the coating on the capillary inner wall.[4] The "one step" method is more compatible with current commercial CE instruments.

However, CIEF performed in commercial CE instruments using mobilization process has problems. Mobilization causes uneven resolution along the capillary column, and makes the pH gradient non-linear so that isoelectric point (pI) values of protein samples are difficult to estimate from their elution times. The mobilization process lengthens analysis time, since focusing takes 2–6 minutes while mobilization usually takes 10–30 minutes.[3–5] During the whole process all protein zones remain focused at the positions where their pI values are the same as pH values.[3–5] Keeping proteins at high concentration and in a state of zero net charge for a long time increases their chance of precipitation. In the "one step" CIEF method, concentrations of carrier ampholytes and additives, and capillary length and sample plug length have to be optimized to adjust mobilization speed in order to obtain the best resolution for different samples.[4,5]

We earlier found that the aforementioned problems arising from the mobilization process can be overcome directly through the use of a new on-line, real-time imaging detector to replace the conventional on-column detectors. Such new detector systems, developed by the present inventors, are the subject of a number of recent publications, which disclose: a universal refractive index gradient imaging detector,[6,7] an optical absorption imaging detector,[7,8] and a fluorescence imaging detector.[9] To accommodate the imaging detector system in the CIEF instruments of this new variety, instrument, short capillaries, 4 cm long were employed. Isoelectric focusing performed in 4 cm long capillaries showed the same resolution as for CIEF performed in 20–60 cm long capillaries.[7] Analyzing a protein sample only takes 2–4 minutes using the imaging detection system. Isoelectric points of components can be determined directly from their positions along the capillary column. The CIEF-imaging detector system was also developed into a multichannel separation and detection method,[10,11] which overcomes the low sample throughput problem of conventional CIEF.

The sample injection procedure used with CIEF-imaging detector instruments is generally as follows. The mixture of sample and carrier ampholytes is first forced into the capillary with a syringe, and then both electrolyte reservoirs connected to the two ends of the capillary are filled with anolyte and catholyte, respectively. Some skill and care are required to ensure that no bubbles are inside the capillary, and that the sample solution inside the capillary is not mixed with the electrolytes in the reservoirs.[7] Each time a sample is changed, the electrolyte in each of the two reservoirs must be changed. This sampling procedure takes about 2–5 minutes for single capillary instruments.

SUMMARY OF THE INVENTION

We realized that CE techniques generally, and most particularly the fast and high through-put separation technique of CIEF, would benefit from the incorporation of means for preparing and introducing the analyte solution into the capillary separation column quickly and the present invention was arrived at to this end.

With a view to attaining this object, the invention comprises an improvement in apparatus for the separation of chemical compounds by capillary electrophoresis using an electrophoretic cell having two electrolyte reservoirs and a capillary separation column having its opposite ends opening into the electrolyte reservoirs, the improvement comprising the provision of the opposite ends of the capillary separation column with semipermeable membrane means operable to permit target analytes from a sample matrix to be introduced on-line into the separation column.

According to a preferred embodiment of the invention, there is provided a capillary separation column whose opposite ends opening into the electrolyte reservoirs are connected to short sections of dialysis hollow fiber, to isolate the analyte sample solution inside the capillary from the anolytic and catholytic solutions while still permitting small ions to migrate freely, so that isoelectric focusing proceeds normally. This arrangement allows samples to be injected conveniently and quickly from one end of the capillary tube with lower-pressure injection means (e.g. a syringe pump) than that needed with conventional apparatus.

Sampling devices for CIEF according to the present invention may use not only a single capillary tube, but also a bundle of capillaries in parallel. One or a plurality of capillary separation channels may be formed and immobilized into a solid substrate, as by etching the channels into a glass slide or silicon wafer and covering the channels over with suitable semipermeable membrane means. This produces a convenient, unitary "cartridge" for carrying out electrophoretic separation and particularly CIEF according to the method of the present invention. In what follows, the term "cartridge" is used to refer to the capillary or capillaries in which electrophoretic separation occurs, together with their attached semipermeable membrane means for connection to the injectioned and outflow ports of the cell.

Sample preparation for CIEF separation usually includes desalting and mixing samples with carrier ampholytes. A high concentration of salt will distort, or even destroy the linear pH gradient during the focusing process.[3] An ideal method of sample preparation for CIEF would be using an on-line desalting carrier ampholytes mixing device which can handle samples with volumes of 1–10 $\mu$L. The creation of such a device was a further object of the invention.

According to a further embodiment of apparatus according to the present invention, there is provided an on-line desalting, carrier ampholyte mixing device, also using semipermeable membrane means, preferably in the form of dialysis hollow fibers. In this arrangement, the dialysis fiber at the injection end of the aforementioned capillary separation column is connected to, or is integral with a longer dialysis hollow fiber through which sample is injected into the capillary. A substantial intermediate portion of the long injection fiber is immersed in a solution of carrier ampholytes contained in a desalting tank or other vessel.

The use of an on-line desalting device according to the present invention is particularly valuable for CIEF separation of protein samples present in only small quantity and stored in high concentration buffer solutions, typically the conditions of availability for sample monoclonal antibodies. High concentrations of salt will distort, or even destroy the pH gradient in CIEF created by carrier ampholytes and, for samples of this kind, conventional desalting methods cannot be used. The novel on-line desalting device of the present invention both effects the desalting and automatically adds carrier ampholytes to the samples. The sample preparation and its introduction into the separation column are thus simplified from existing methods in CIEF.

The method of the invention can be used for on-line coupling of capillary electrophoresis to other separation methods such as HPLC, to produce two-dimensional information. In such applications, the membrane can be used to remove low molecular weight components from the mobile phase prior to focusing. Because of the simplicity of the system, it is contemplated to use a multi-channel CIEF device in which the separation column comprises channels integrally etched onto a single glass slide or silicon wafer and coated over by an appropriate semipermeable membrane, so that several samples can be desalted, mixed with the CIEF buffer solution, and injected into a multi-channel CIEF device.

BRIEF DESCRIPTION OF THE DRAWINGS

The invention will now be described further with reference to the accompanying drawings, in which.

DESCRIPTION OF PREFERRED EMBODIMENT

Instrumental Procedure

Figure 1:
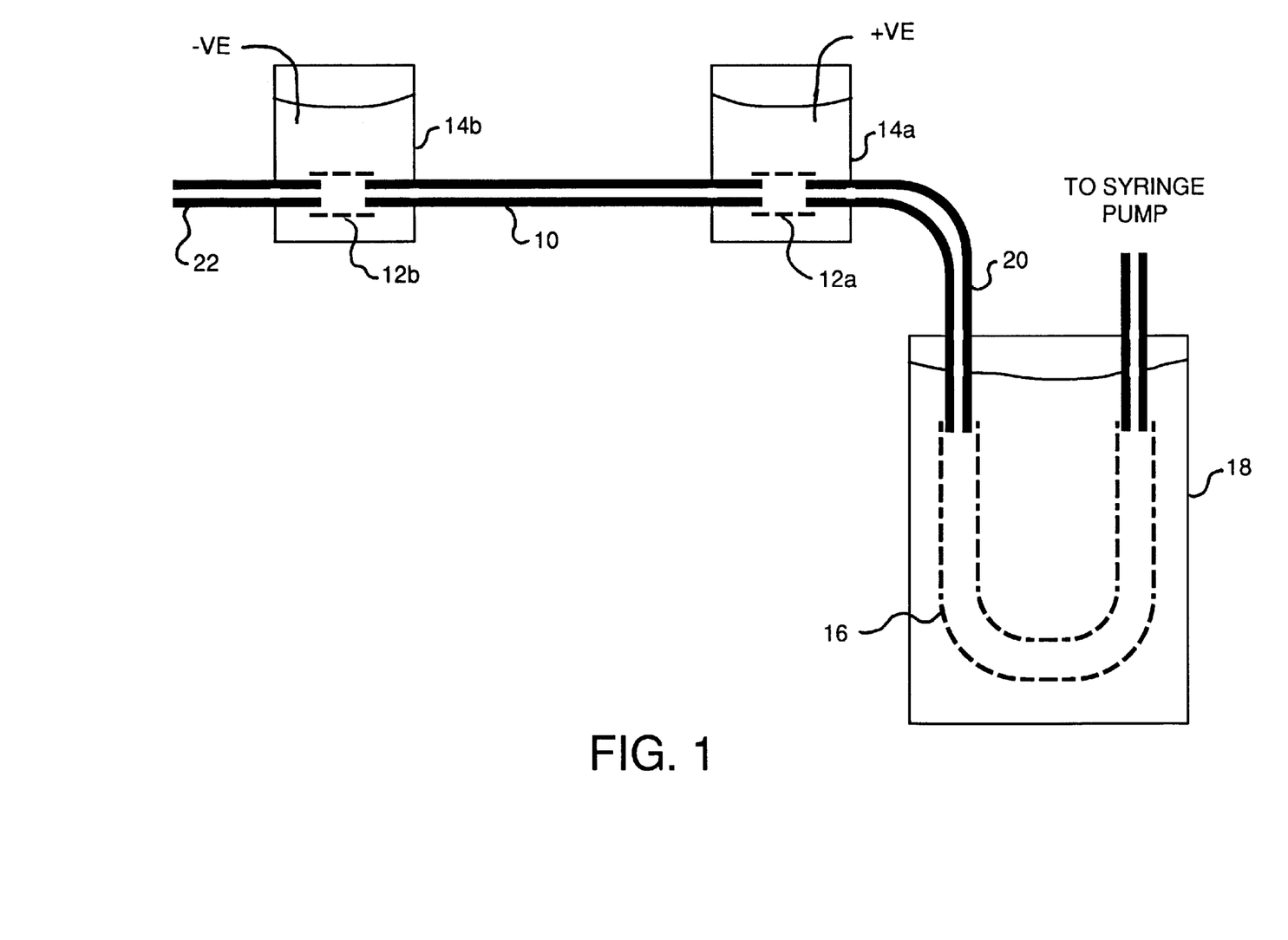
FIG. 1 is a schematic representation of a capillary separation column and associated on-line desalting device for use in CIEF according to a preferred embodiment of the present invention.

The configuration of the capillary cartridge for use in CIEF, as shown in FIG. 1, is similar to that used in previous experiments.[7] The separation column 10 is a 4 cm long, 75 $\mu$m i.d., 150 $\mu$m o.d., silica capillary (Polymicro Technologies, Tucson, Ariz.). The coatings on the outside of the capillary were removed for detection. The capillary inner wall was coated with non-cross-linked acrylamide to eliminate electroosmotic flow in the reported manner known in the art.[2] The two ends of the capillary are connected to two pieces of 3 mm long dialysis hollow fibers 12a and 12b (Spectrum Medical Industries, Inc., Los Angeles, Calif.). The i.d. of each fiber is 150 $\mu$m and the o.d. is 170 $\mu$m. Its molecular weight cut-off value is 9,000. The two sections of fiber are inserted into the two electrolyte reservoirs, one 14a filled with analyte, 10 mM $H_3PO_4$, and the other 14b with catholyte, 20 mM NaOH.

As shown in FIG. 1, the desalting device consists of a 10 cm long dialysis fiber 16 (injection fiber) immersed in an 100 mL beaker 18 containing 4% carrier ampholytes solution. One end of the injection fiber 16 was connected to the short fiber tip 12a of the inlet of the separation column 10 through a 75 $\mu$m i.d. capillary 20, and the other end was connected to a low-pressure (~50 p.s.i.) syringe pump (not shown). Protein samples were injected into the separation column 10 through the desalting device, flowing out of the device through capillary section 22, connected to fiber section 12b.

The detection system has an absorption imaging detector using a CCD camera. The design of the detector is explained in greater detail in an earlier publication[11] and also in U.S. Pat. No. 5,395,502 (Pawliszyn and Torres) the disclosure of which is incorporated herein by reference. A monochromatic light beam at 410 nm was obtained by passing the light beam from a W lamp through a 410 nm, 40 nm bandpass filter. The light beam was directed through the capillary column by a bundle of 300, 200 $\mu$m o.d. optical fibers.

Reagents

All chemicals were reagent grade. Hemoglobin samples (Hemo AFSC, Hemo $AA_2$ and Hemo AS) were purchased from Helena Laboratories, Beaumont, Tex. Horse myoglobin, and carrier ampholytes (Pharmalyte 3–10) were obtained from Sigma Chemical Co. Solutions were prepared in deionized water, and filtered using 0.2 $\mu$m pore size cellulose acetate filters (Sartorius, Gottingen, Germany) prior to use.

Desalting and Isoelectric Focusing Process

First, the two reservoirs 14a and 14b at the ends of the capillary column 10 were filled with anolyte and catholyte, respectively, and sample was pumped into the desalting device. The carrier ampholytes solution in the 100 mL beaker 18 was stirred by means of a magnetic bar. Small salt molecules in the sample were washed away through the wall of the dialysis hollow fiber 16 in the beaker, and at the same time small carrier ampholyte molecules (molecular weights less than 3,000 D) were added to the sample through the wall of semipermeable hollow 16. The flow rate was adjusted to about 1 $\mu$L/min. A 500 V DC voltage was applied to the two reservoirs, and current passing through the separation column was monitored during the desalting process.

When the current dropped to about 1 $\mu$A in 1–2 minutes, the syringe pump was stopped, and the capillary column 10 was blocked at the other end to stop the hydrodynamic flow inside the column. Then, the separation voltage (3 kV) was turned on. The focusing process was monitored by the absorption imaging detector, and the detection was completed when focusing finished. The total analysis time is usually 2–4 minutes. After an analysis, the whole system was washed with deionized water for about 20 seconds, and it was ready for the next sample.

Results and Discussion

The dialysis hollow fibers 12a and 12b in the cartridge isolate the sample solution inside the capillary 10 from the electrolytes in the reservoirs. However, small chemical species, such as $H^+$ and $OH^-$ ions, can pass through the wall of the hollow fiber freely. Thus, isoelectric focusing can take place normally inside the capillary held by the cartridge. With such a cartridge, sample injection is a simplified procedure. Sample solution can be injected from one end of the capillary column without withdrawing the electrolytes inside the two reservoirs, a procedure much more convenient than the sample injection method associated with conventional "one step" or "two step" CIEF performed in commercial CE instruments.

Figure 2:
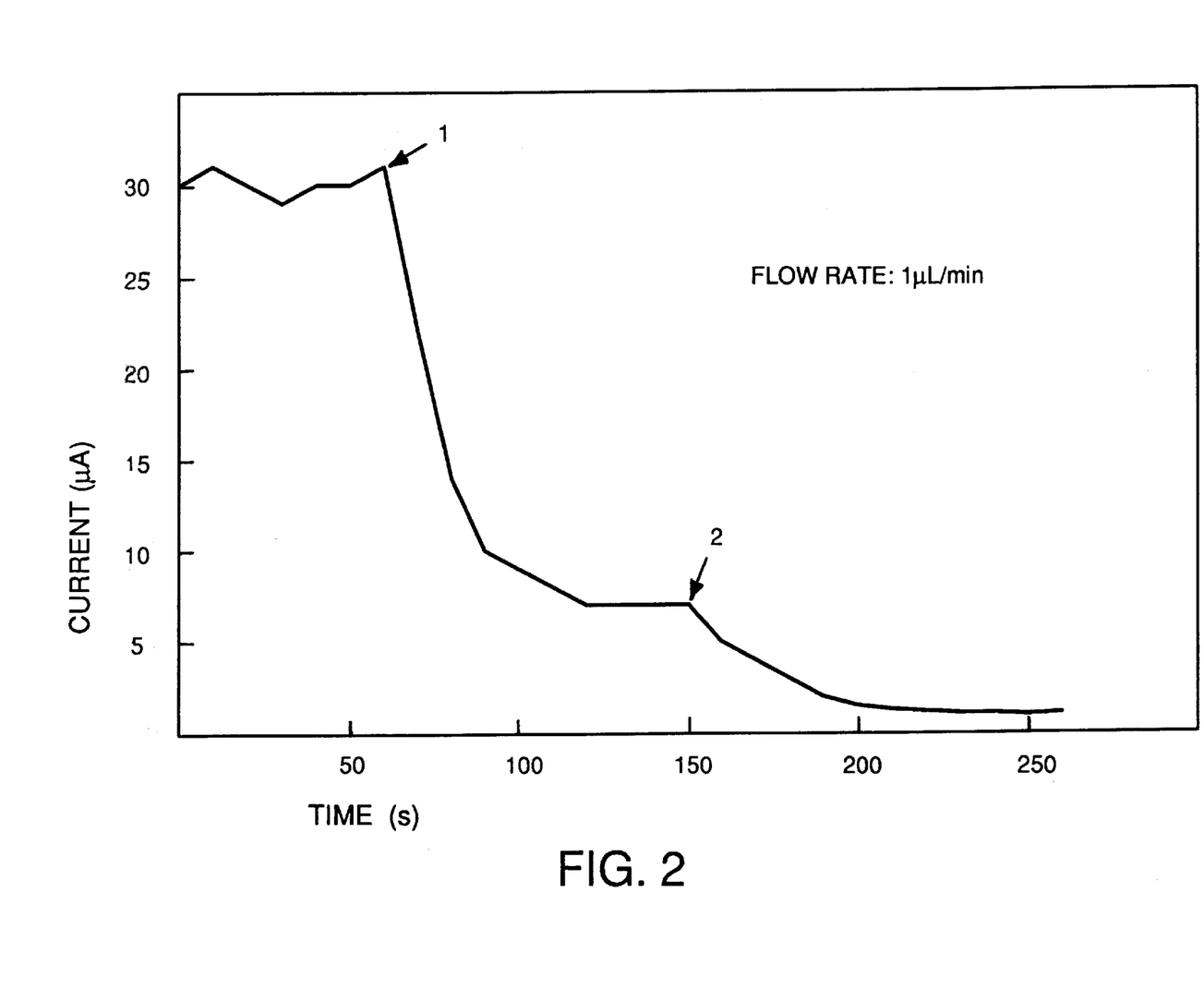
FIG. 2 is a graphical representation of the decrease in time of the current developed at a fixed voltage in a separation column with associated desalting device according to the present invention, with a myoglobin solution sample, illustrating the efficiency of the desalting device.

The efficiency of the desalting device of the present invention was investigated in an experiment using myoglobin dissolved in 100 mM Tris buffer as the sample. The salt concentration in the sample during desalting process was monitored by measuring the current passing through the separation column. As shown in FIG. 2, when there is no solution in the 100 mL beaker, the current passing through the capillary is about 30 $\mu$A for the 500 V voltage applied. This current shows that the 100 mM salt concentration is too high. Usually, the voltage applied to the 4 cm long capillary during the focusing process is 3–4 kV. The current under that voltage would have been about 0.2 mA, which is high enough to boil the solution inside the 75 $\mu$m i.d. capillary. The linear pH gradient would also be destroyed by the high concentration of salt. Isoelectric focusing can not be performed with this salt concentration.

Then, a solution of 4% carrier ampholytes is added to the beaker (arrow 1 in FIG. 2). The current drops quickly from 30 $\mu$A to about 8 $\mu$A and stabilizes in about 1 minute. This result shows that diffusion of salt from inside the fiber to outside the fiber is very fast, as expected, due to the narrow diameter of the dialysis hollow fiber. Thus, passing a sample through the fiber before it enters the separation column can desalt the sample effectively. The residual of salt in the sample can be better washed away by stirring the solution inside the beaker. The arrow 2 in FIG. 2 indicates the time when the stirring starts. After the stirring starts, the current reduces to 1 $\mu$A and stabilizes in 50 seconds.

In the device, the desalted protein sample is also mixed with carrier ampholytes in the 10 cm long dialysis hollow fiber 16 immersed in the 100 mL beaker 18. So, after the current stabilizes, the pump can be stopped, a 3 kV DC voltage applied, and the sample focused inside separation column 10 between the two electrolyte reservoirs. Since in the instrument, a real-time absorption imaging detector is used, the focusing process can be monitored, and detection finishes when focusing is complete, which only takes about 3 minutes. The whole analysis time for a sample using this instrument is less than 4 minutes including the desalting procedure. This is the first report of an on-line desalting and carrier ampholyte mixing device for CIEF.

The CIEF instrument can be used for fast screening of abnormal hemoglobins, such as hemoglobins from sickle cell anemia patients. Also, variants separated by CIEF can be determined quantitatively with this instrument by their absorption peak areas, such as determining the ratio of variants A and $A_2$ by the ratio of their peak areas shown in FIG. 3.[12]

Isoelectric focusing performed in a cartridge embodying our invention has advantages for reproducible sample injection over conventional CIEF and other CE methods. In CE and CIEF with "one step" methods the length of the sample plug has to be accurately (standard deviation less than 10%) controlled for quantitative determination. Usually, the plug is introduced into the capillary by hydrodynamic or electrokinetic methods,[2] which cannot be easily controlled when a narrow capillary is used. However, by the use of our cartridge, the amount of sample injected into the capillary does not need to be controlled. When the DC voltage is turned on for the cartridge shown in FIG. 1, only part of sample between the two dialysis hollow fibers is focused. The sampling volume equals the capillary column volume between the two fibers, which guarantees the high accuracy in sampling volume. Preliminary results of quantitative determinations of proteins using our new instrument have exhibited high precision.

Figure 3:
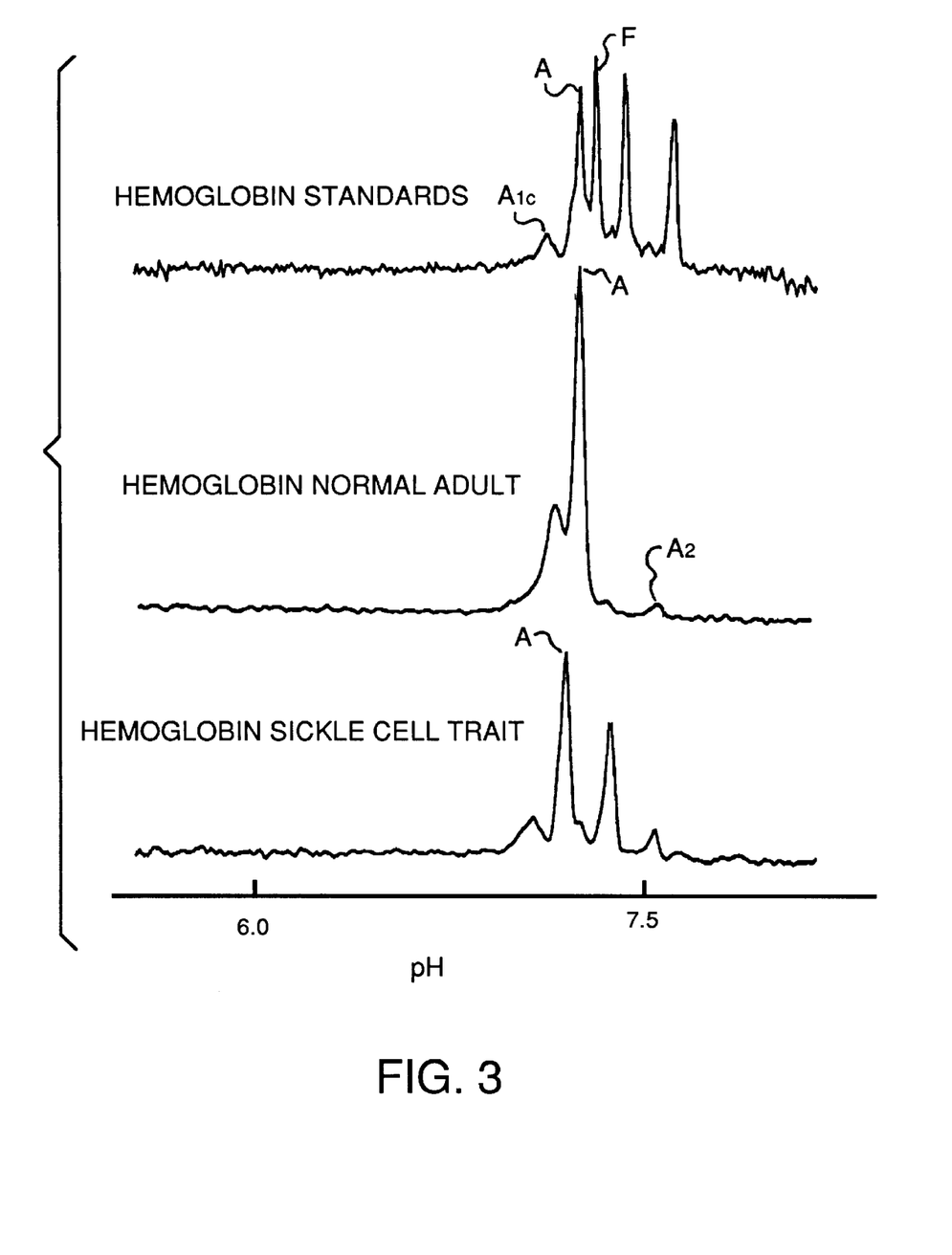
FIG. 3 shows electropherograms of three hemoglobin samples injected consecutively into the CIEF instrument of FIG. 1.

FIG. 3 shows electropherograms of three hemoglobin samples injected consecutively. The reproducibility of focusing patterns with this instrument is good for the consecutively injected samples, which shows that the salts in the sample are adequately washed away, and that the carrier ampholytes are effectively mixed into the sample. All three samples were analyzed by the instrument shown in FIG. 1 in 15 minutes, including sampling times. This speed is about 3 times faster than that of a conventional CIEF analysis.[3–5] The resolution, when the pH 3–10 carrier ampholytes are used, is estimated to be 0.02 pH units from the distance between hemoglobin A and F (pI difference between them is 0.05 pH units).

Figure 4:
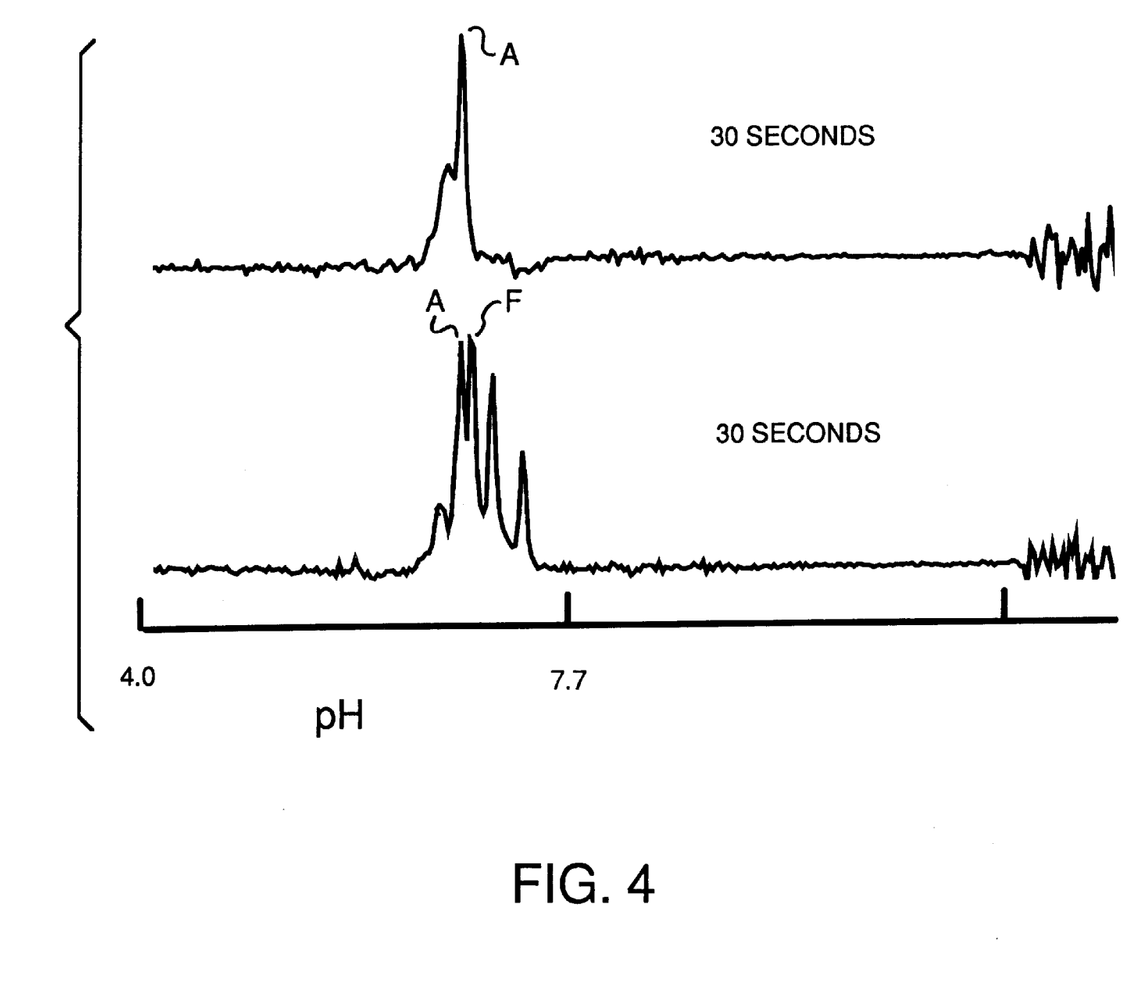
FIG. 4 shows electropherograms of two hemoglobin samples run consecutively on the CIEF apparatus of FIG. 1, but with a capillary separation column only one cm long.

The separation speed of CIEF can be further increased with this new capillary cartridge since its speed is no longer limited by sampling. Fast CIEF may be useful for two-dimensional separations (2-D separation). 2-D separation usually requires that sample injection intervals to the second separation step be short and the second step be a fast one, so that the second separation can sample a peak eluted from the first separation dimension several times across the peak's width.[13] Although the analysis time of the CIEF with the cartridge and imaging detector reaches 2–4 minutes for a sample, this speed is still not high enough for CIEF to couple with high performance liquid chromatography (HPLC) methods since the peak widths of HPLC are usually in the few minutes range. With the new cartridge design, the speed of CIEF can be further increased using an even shorter capillary column. FIG. 4 shows electropherograms of two hemoglobin samples separated consecutively in a 1 cm long capillary using the design shown in FIG. 1. The focusing time is only 30 seconds, and analysis time for the two samples is 2 minutes including the sampling for the two runs. A resolution of the separation is about 0.05 pH units, since hemoglobin A and F have a 0.05 pH unit difference. This resolution can be enhanced by using narrower pH range carrier ampholytes[11], such as pH 6–8, if the range of the sample's pI values are known. This speed allows CIEF to be coupled with HPLC preparation in a two-dimensional separation scheme.

OTHER APPLICATIONS

The general approach taken in the various aspects of the present apparatus and method is to apply membrane technology in the on-line introduction of samples to capillary electrophoretic separation cells. The semipermeable membrane serves the function both of removing small molecules from the sample (the desalting process), as well as to introduce small molecules from the external vessel through the membrane (adding ampholytes or hydronium ion/hydroxide ion). The principle is useful in many other capillary electrophoretic techniques in addition to the specific example of CIEF outlined above.

Thus, the device shown in FIG. 1 could be used in capillary zone electrophoresis. In CZE separation, the capillary column is filled with buffer, and samples may be introduced into the capillary column from the inlet of the column or from either of the electrolyte reservoirs, through membranes such as hollow fibers. This introduction can be done using pressure or by the application of a voltage pulse to the reservoir.

The capillary cartridge of FIG. 1 could also be employed in capillary gel electrophoresis and to electrophoresis carried out in packed columns. CIEF can be performed in a gel-filled capillary by first passing the mixture of the sample and gel through the membrane placed in the container with ampholyte solution, which allows desalting of the mixture and addition of the ampholyte to be sample/gel mixture. The capillary separation column is filled with a mixture of protein sample, carrier ampholytes and gel (polyacrylamide gel or agarose gel). After the gel is polymerized in the interior of the capillary column, a separation voltage is applied to the two electrolyte reservoirs to begin the process of isoelectric focusing. In carrying out capillary zone electrophoresis in a gel-filled capillary column, set up as in FIG. 1, sample plugs could be introduced into the capillary column from either inlet of the column or through the membrane hollow fibers inside the electrolyte reservoirs, using electrokinetic mobilization.

The capillary separation column of FIG. 1 could be a packed column. Any packing material useful in HPLC might be used to pack the electrophoretic column in apparatus according to the present invention. A solution can pass through the packed column under pressure, so that CIEF sample loading procedures described above are applicable to packed column CIEF as well. Further sample introduction procedures used in conventional CZE might also be applied to a packed column in a cartridge as shown in FIG. 1, where the apparatus of FIG. 1 is used to carry out packed column CZE instead of the CIEF process described above.

On the other hand, in application of semipermeable membranes to the CZE technique rather than CIEF, a simpler membrane configuration than that shown in FIG. 1 might be used. Only a short piece of membrane would be needed at the front on the separation capillary, and it could be used in either of two ways:

Firstly, the narrow plug of sample (e.g. blood) is passed through the centre of the fiber to the capillary. During this process (entirely analogous to the desalting stage of CIEF), the low molecular weight species are removed from the sample and required buffer components are added to it. Then the plug is delivered to the front of the column for separation. This permits the separation of large molecules present in the sample, as where it is proteins which are the analytes.

Secondly, in a "reversed" process in which the analytes are low molecular weight species, sample would be added to a vessel containing the membrane and low molecular analytes will permeate through the membrane for separation by capillary zone electrophoresis. Membrane dimensions must be sufficiently small to allow introduction of the sample as a narrow plug. This second, variation of the CZE process using semipermeable membrane-based sampling means according to the present invention is contemplated for the separation of low molecular weight species present in a sample, particularly drawn blood with the target analyte being, for example, drugs and their metabolites.

The choice of a membrane of a hollow fiber geometry is preferred and convenient, particularly in the application to CIEF, as a membrane of this form is self-supporting and conveniently constructed. The on-line use of semipermeable membranes in CIEF and other kinds of capillary electrophoresis might conveniently involve different geometries of semipermeable membrane. Thus, with a cartridge according to the present invention, in which the capillary channels are permanently etched into a silica or silicon substrate, coating the assembly of capillary openings at either end of the cartridge with flat pieces of semipermeable membrane affords a convenient way of interposing a semipermeable membrane between the separation columns and the cell reservoirs.

Figure 5:
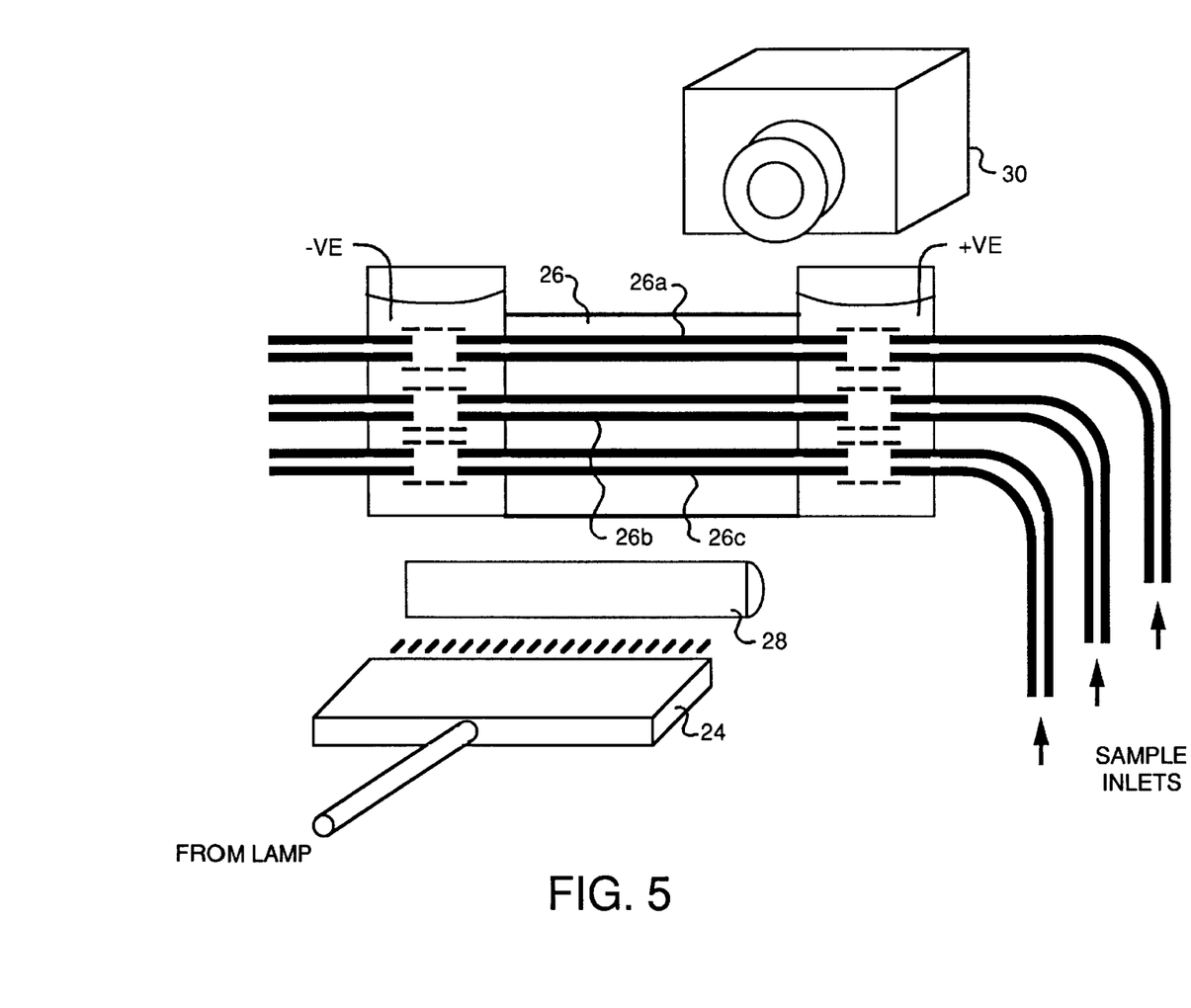
FIG. 5 schematically represents a CIEF instrument in which the separation column is a multicapillary cartridge of capillaries including dialysis hollow fiber sections according to the present invention.

Since the desalting device and the sample injection step for the cartridge could be automated with an autosampler, CIEF could be performed in multiple capillaries fixed on a single cartridge automatically, including sample preparation. Multicapillary CIEF can be detected with the absorption imaging detector.[11] FIG. 5 shows structure of a multicapillary instrument, which is similar to that with a single capillary instrument and can be coupled with a multichannel on-line desalting device. The beam from a suitable light source (not shown) is sent into a bundle of optical fibers 24, and then is projected onto the capillary cartridge 26 by a 5 cm focal length cylindrical lens 28. The sample zones focused inside the capillaries are monitored by CCD camera 30. In the present experiment, three capillaries 26a, 26b and 26c are used in the instrument, although technically more than three capillaries could be in the cartridge. Advantageously, parallel capillary channels have been formed by etching a glass or silicon plate.

The use of multicapillaries greatly increases the sample throughput of CIEF, making it comparable to gel slab isoelectric focusing in which several samples and standards can be separated in different channels simultaneously. But the speed of CIEF is much faster than that of a gel slab isoelectric focusing which needs hours for a separation.

Using the present invention, sampling procedure for the three capillaries takes less than 2 minutes even manually. This time could be reduced still further by using an autosampler. After three samples are injected into the capillaries, the separation DC voltage is applied to the two electrolyte reservoirs, and focusing begins in the three capillaries. Focusing and detection is completed in all three capillaries in 3 minutes.

Figure 6:
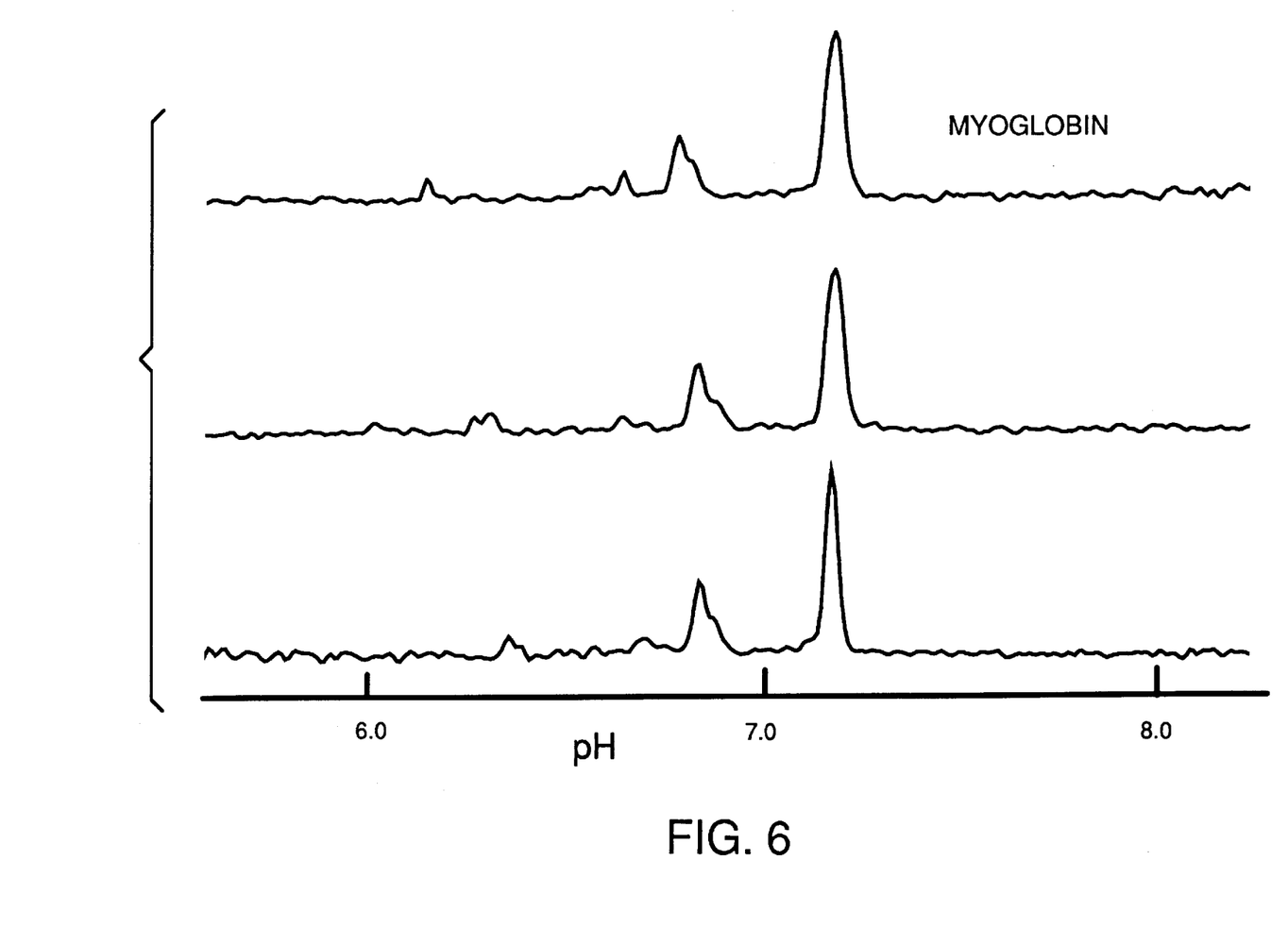
FIG. 6 shows electropherograms of 3 myoglobin samples separated using a multiple capillary cartridge of the kind represented in FIG. 5, detected by an absorption imaging detector operated at 410 nm wavelength.

FIG. 6 shows an example application of the multicapillary CIEF instrument. The separated zones inside the three capillaries are monitored by the absorption imaging detector operated at 410 nm. Three replicate myoglobin samples are focused in the three capillaries. The whole analysis time for all three samples including sampling procedure is only about 5 minutes. The result shows good reproducibility of the focused pattern. Because of the good reproducibility, unknown samples could be run with a standard simultaneously, and zone in the unknown sample can be identified by comparing their positions along the capillary with those in the standard. This comparison between a standard and a sample is difficult with a conventional single channel CIEF instrument.

From the foregoing it will be seen that the present invention simplifies and to a degree automates the sample preparation and introduction for CE and, most particularly, for capillary isoelectric focusing. Membrane technology is applied to produce on-line desalting, the introduction of ampholytes and the focusing of proteins contained in the sample. The method can be used for on-line coupling. Other separation techniques, such as HPLC, used jointly with CIEF can produce two-dimensional information. In that application, the membrane can be used to remove low molecular weight components from the mobile phase prior to isoelectric focusing. The system is simple and can conveniently be integrated onto a single glass slide by means of etching and polymer coating technologies.

It is not intended by the description of embodiments of the invention for illustrative purposes thereby to impose a limitation on the invention to the specific constructions shown and described herein. Various modifications apparent to those skilled in the art may be made without departing from the invention defined in the appended claims.

REFERENCES (1) Wehr, T.; Zhu, M.; Rodriguez, R.; Burke, D.; Duncan, K. Am. Biotechnol. Lab. 1990, 8, 22–29.
(2) Hjerten, S.; Zhu, M. J. Chromatogr. 1985, 346, 265–270.
(3) Zhu, M.; Rodriguez, R.; Wehr, T. J. Chromatogr. 1991, 559, 479–488.
(4) Mazzeo, J. R.; Krull, I. S. Anal. Chem. 1991, 63, 2852–2857.
(5) Thormann, W.; Caslavska, J.; Molteni, S.; Chmelik, J. J. Chromatogr. 1992, 589, 321–327.
(6) Wu, J.; Pawliszyn, J. Anal. Chem. 1992, 64, 224–227.
(7) Wu, J.; Pawliszyn, J. Anal. Chem. 1994, 66, 867–873.
(8) Wu, J.; Pawliszyn, J. J. Liq. Chromatogr. 1993, 16, 1891–1902.
(9) Wu, J.; Pawliszyn, J. Am. Lab. 1994, October, 48–52.
(10) Wu, J.; Pawliszyn, J. Electrophoresis, 1993, 14, 469–474.
(11) Wu, J.; Pawliszyn, J. Analyst, 1995, 120, 1567–1571.
(12) Li, S. F. Y. Capillary Electrophoresis, Principles, Practice and Applications, Elsevier: Amsterdam, 1992.
(13) Bushey, M. M.; Jorgenson, J. W. Anal. Chem. 1990, 62, 978–984.

We claim:

1. An apparatus for the separation of chemical compounds by capillary electrophoresis, having an electrophoretic cell with two electrolyte reservoirs and a capillary separation column with its opposite ends opening into said reservoirs, wherein the improvement comprises semipermeable membrane means at said opposite ends of the capillary separation column that permit a liquid sample containing target analytes to be introduced on-line into the separation column, while preventing analyte from escaping into the electrolyte in said reservoirs but permitting the transfer of selected chemical species between the electrolyte and said liquid sample.

2. The improvement according to claim 1, wherein said semipermeable membrane means comprises a section of semipermeable hollow fibres attached to at least one end of the capillary separation column, with the interior lumen of the fibre in fluid communication with the interior of said capillary separation column.

3. The improvement according to claim 2, wherein said apparatus is for the separation of chemical compounds by capillary isoelectric focusing.

4. The improvement according to claim 1, wherein said apparatus for the separation of chemical compounds by capillary electrophoresis comprises a plurality of capillary separation columns.

5. The improvement according to claim 4, wherein said capillary separation columns are channels formed in a solid substrate.

6. The improvement of claim 5, wherein said solid substrate is a glass plate.

7. The improvement of claim 5, wherein said solid substrate is a silicon wafer.

8. The improvement of claim 2, wherein the apparatus includes an on-line desalting carrier ampholytes mixing device, comprising an elongate dialysis membrane in the form of a hollow fiber connected at one end thereof to the inlet of said capillary separation column and at the other end thereof to sample delivery means, an intermediate portion of said elongate fiber being immersed in a supply of carrier ampholytes.

* * * * *